United States Patent [19]

MacDonald et al.

[11] Patent Number: 5,776,170
[45] Date of Patent: Jul. 7, 1998

[54] ELECTROTHERAPEUTIC APPARATUS

[76] Inventors: Alexander John Ranald MacDonald, 19 Richmond Hill, Bristol, Great Britain, BS8 1BA; Timothy William Coates, Ash Green Cottage, Front Street, Churchill, Bristol, Great Britain, BS19 5NB

[21] Appl. No.: 500,843
[22] PCT Filed: Feb. 4, 1994
[86] PCT No.: PCT/GB94/00211
  § 371 Date: Sep. 18, 1995
  § 102(e) Date: Sep. 18, 1995
[87] PCT Pub. No.: WO94/17855
  PCT Pub. Date: Aug. 18, 1994

[30] Foreign Application Priority Data

Feb. 5, 1993 [GB] United Kingdom ............ 9302335

[51] Int. Cl.[6] .................................................. A61N 1/36
[52] U.S. Cl. ............................................................ 607/46
[58] Field of Search ........................................ 607/72, 46

[56] References Cited

U.S. PATENT DOCUMENTS 4,554,923  11/1985  Batters ................................... 607/46

Primary Examiner—Scott M. Getzow
Attorney, Agent, or Firm—Dann, Dorfman, Herrell and Skillman

[57] ABSTRACT

An apparatus for producing analgesia through electrical stimulation is disclosed wherein the apparatus comprises two or more electrodes adapted to supply electrical signals to two or more locations on the surface of a body overlying the central nervous system. The apparatus further comprises signal generating means connectable to the electrodes which supply electrical pulses featuring rapid rising and falling phases at parameters of pulse width, frequency and amplitude such that analgesic effects tend to be stimulated in the central nervous system or its adnexa, while stimulating peripheral nerves that lie between the electrodes and the central nervous system to a lesser extent or not all.

8 Claims, 1 Drawing Sheet

ELECTROTHERAPEUTIC APPARATUS

FIELD OF THE INVENTION

This invention relates to the field of electrotherapy, and provides apparatus for a particular application of such therapy.

BACKGROUND OF RELATED ART

The nervous system is able to respond to an interrupted DC or alternating current, provided the repetition rates or frequencies do not exceed values that vary according to the particular properties of each class of nerve. Severe dull or aching pain is associated with the firing of unmyelinated or C fibres (Class IV). These fibres cannot follow a maintained frequency higher than about 2 Hz. In addition they have a high threshold and normally only respond to excessive mechanical or thermal stimulation that injures cells. Sharp pain is associated with the firing of Aδ (Class III) fibres. They cannot follow electrical stimulation rates higher than about 50–80 Hz. There is also a class of nerve fibres that may faithfully follow electrical stimulation at rates up to approximately 800 Hz; these are called Aβ or Class II fibres. The Class II receptors have a low threshold to any form of stimulation and respond to such innocuous events as movement or light touch.

Melzack and Wall (1965) and Wall (1986) describe how analgesia can be produced when the Class II or Aβ fibres are stimulated electrically at 100 Hz, a frequency that none of the other nerves can follow.

Wall (1986) produced these effects by applying the current through needles inserted into the patient's nerves. To avoid the inconvenience and possible complications of inserting needles into nerves, surface electrodes were later employed, leading to the term Transcutaneous (Electrical) Nerve Stimulation (TNS or TENS).

Woolf (1989) has reviewed the use of these devices, and described their electrical parameters. The usual TENS machine develops a pulse, whose width can be varied from 50–500 μs, employing a current whose amplitude can be increased from 0–50 mA, and whose frequency is generally 80 or 100 Hz.

The TENS pulse width (50–500 μs) is intended to be sufficiently long in duration to excite Aβ nerves to cause a painless tingling at low voltage.

In known TENS devices, the maximum current density and sensation tends to occur in tissues immediately underlying the electrodes, and only a proportion of the applied current reaches the deep tissues. Thus, when choosing a comfortable level of stimulation, the patient is first guided by sensations arising from peripheral nerve stimulation in tissues immediately below the electrodes. If the amplitude is increased to try and produce more current in the deep tissues, pain may be produced when there is sufficient voltage to recruit Aδ fibres. This tends to limit the amplitude of TENS that can be tolerated by a patient.

Although tingling produced by the TENS method is usually painless and reasonably well accepted by patients, it tends to produce a rather short-lived, localised region of analgesia, as each electrode probably stimulates a few hundred Aβ fibres in the immediate vicinity of the electrodes. Accordingly, in patients where there may be several large areas of the body in pain, there is a need to improve the method to produce a more long-lasting and generalised form of analgesia.

In an attempt to fire more Aβ fibres, wire electrodes have been implanted in the spinal canal to stimulate the central nervous system itself, in particular the dorsal columns (tracts through which the Aβ fibres pass up and down the spinal chord). This is called Dorsal Column Stimulation, and is reviewed by Krainick et al (1989). The present technique employs small bare tips of otherwise insulated wires, probably stimulating a few thousand Aβ fibres. However, the implantation of the wires involves surgery and the risk of infection along the track of the wires.

SUMMARY OF THE INVENTION

In order to avoid the risks of implanting electrodes in direct contact with the central nervous system, U.S. Pat. No. 3,835,833 (Limoge) describes application to a patient's head of intermittent 4 ms blocks of high frequency current (166 KHz), each block being repeated 100 times per second, designed to penetrate the brain from two surface electrodes. Breaking the signal up into these trains tends to excite peripheral nerves and Stinus et al (1990) have observed that such stimulation only raises pain thresholds when opiates have been administered.

The present invention provides an apparatus for producing electrical stimulation wherein the apparatus comprises two or more electrodes adapted to supply electrical signals to two or more locations on the surface of a body overlying the central nervous system, wherein the apparatus further comprises signal generating means connectable to the electrodes which supply electrical pulses having rapid rising and falling phases at parameters of pulse width, frequency and amplitude such that analgesic effects tend to be stimulated in the central nervous system while stimulating peripheral nerves that lie between the electrodes and the central nervous system to a lesser extent or not all.

Thus the present invention allows analgesic effects all over the body to be initiated in the central nervous system, in particular the spinal cord, preferably without requiring prior medication or causing any discomfort. We refer to this as Transcutaneous Spinal Electroanalgesia (TSE), and it depends on electrical signal being applied via surface electrodes to initiate changes in the central nervous system, for instance the spinal cord lying some 5 cms deep to the skin, without exciting the peripheral nerves in the intervening tissues.

DETAILED DESCRIPTION OF THE INVENTION

Figure 1:
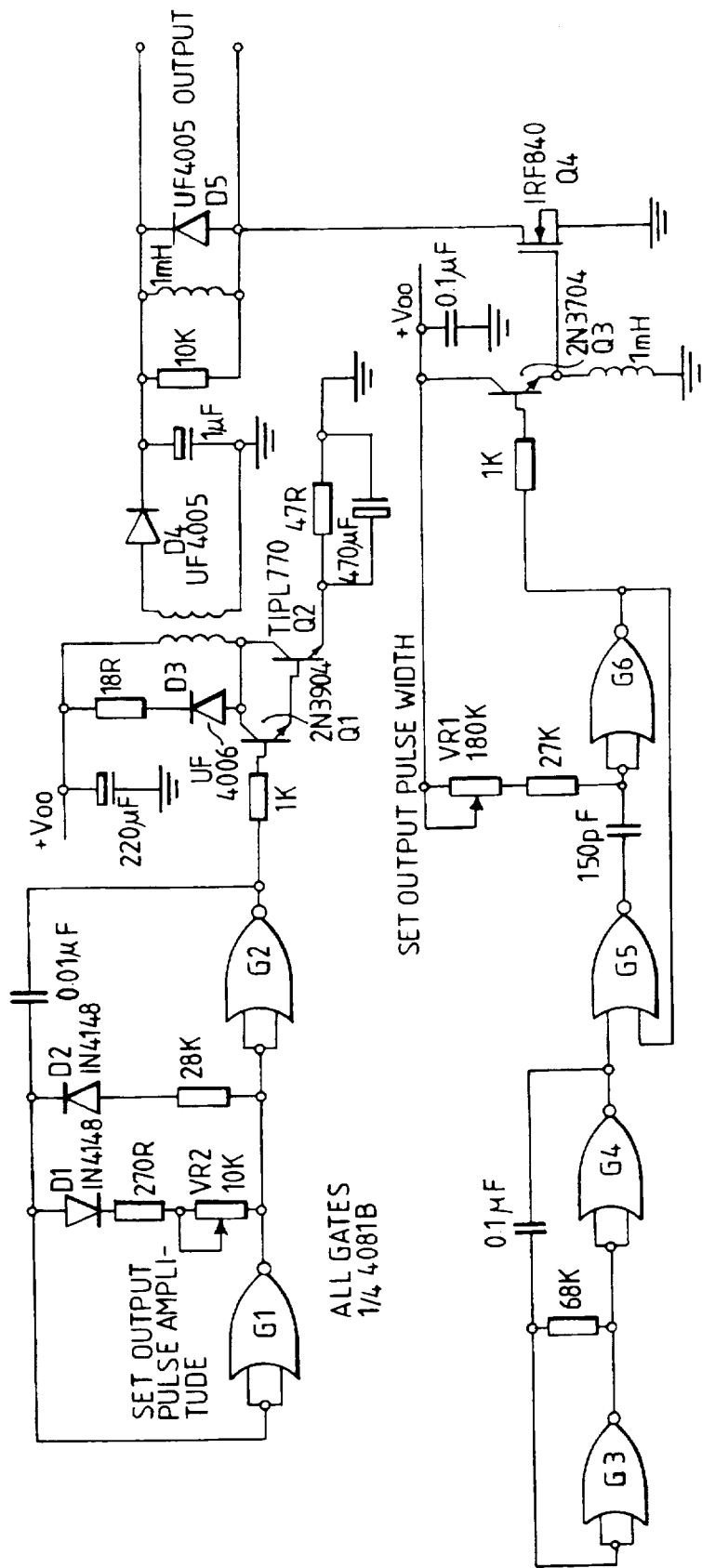
FIG. 1, the sole drawing FIGURE, shows a schematic representation of an apparatus for producing analgesia through electrical stimulation in accordance with the present invention.

In the context of the present invention, the term "central nervous system" should, except where the context demands otherwise, be interpreted to include the brain and spinal cord, together with their adnexa, ie other neural tissues that are classed as part of the peripheral nervous sytem, but are in close anatomical proximity to the central nervous system, eg the ganglia, autonomic or somatic, such as the dorsal root ganglia.

The approach we have adopted here accords with apparent stimulation of the spinal cord by summation. This may be explained as follows.

The minimum current required to stimulate each class of nerve has been studied (Brinley 1974, pages 34–36). This minimum value is called a threshold stimulus. To elicit a response in a nerve, the threshold electrical stimulus must be applied for a finite time; the weaker the current, the greater the time required for stimulation. If the strength of the stimulating current is below a minimum quantity, the current may flow indefinitely without exciting the nerve. On the other hand, a current lasting less than a minimum length of time will not stimulate, however great its amplitude. There are great differences, however, between the responsiveness of the various classes of nerves to periods of stimulation at various amplitudes. For example, Li et al (1976, page 72, FIG. 4) have shown (in a peripheral nerve of the cat) the minimum length of time required to stimulate A$\beta$ fibres with a current of 0.2 mA is 6 μs; whereas at the same amplitude A$\delta$ fibres and C fibres require periods of stimulation at least a hundred times as long in duration (i.e. in excess of 600 μs).

When an electrical stimulus is subthreshold (i.e. too brief in duration and amplitude to cause a nerve to fire), it still has an effect on the nerve that may make it more responsive to another stimulus. Thus, the phenomenon of summation occurs, when two or more subthreshold stimuli combine to cause excitation.

Spatial summation may be described in the following way. Although the effects of subthreshold electrical stimulation of a nerve are at their greatest in the immediate vicinity of the electrode, changes also take place in adjacent regions. Thus simultaneous subthreshold stimulation in two or more loci are able to summate to produce excitation.

Whether summation is the mechanism of action or not, TSE avoids stimulating peripheral nerves, yet provides a signal that produces effects in the central nervous system, possibly by stimulating vesicles to release opioids such as metenkephalin or dynorphin.

1. The TSE Stimulator

One embodiment of the present invention employs a single pair of electrodes, typically having a size of 4×4 cm. Usually one electrode is placed on the skin of the mid-line of the back overlying one end of the portion of spinal cord that requires stimulation, while the second is placed at the other end. In a similar manner, however, more than two electrodes could be arranged over the spinal cord.

We have also found that when electrodes are placed on either side of the neck, analgesic effects may be obtained in the cranium. We have also attached electrodes to the skin overlying the brain, and have obtained analgesic effects depending on various parameters of stimulation, but side effects such as flashes of light and a metallic taste are sometimes produced. Accordingly, the placement of the electrodes on regions overlying the spinal cord is preferred as this has not produced any known side effects.

Although in general electrodes are placed on the surface of a body, in some circumstances it may be desirable to implant the electrodes. This is generally not preferred due to the risk of infection associated with this procedure.

In order to stimulate the spinal cord without producing discomfort, we have studied the effects of a TSE stimulator designed to produce a pulses having both rapid rise and fall phases. This device has been used in the following experiments, described below with reference to the circuit diagram shown in FIG. 1. It features an output pulse which is variable in amplitude between approximately 450V or less and has a pulse width typically of 10 μs or less, eg 1.5–4 μs. This pulse is repeated at intervals of approximately 4 μs or more. The stimulator is designed to give pulses having rapid rise and fall phases, eg a substantially rectangular pulse wave, even at maximum amplitude when driving 4×4 cm stick-on skin electrodes. Both monopolar and bipolar pulses having rapid rise and fall phases can be applied to a patient via the electrodes.

This ability to control the shape of the output pulse even when driving a capacitive load together with the narrow pulse width used for stimulation constitutes the major differences between this TSE stimulator and conventional TENS-type stimulator machines. In the latter devices, the shape of the output wave is substantially dominated by the load impedance of the body, and the minimum TENS pulse width is typically 100 times longer than TSE. In addition, when applied at the normal TENS frequency of 100 Hz the amplitude of the pulse produced by the TSE stimulator is higher than that of the conventional TENS machines i.e. typically 180V, but even up to 1 kV or more, compared to 35–50V. The narrow 1–10 μs TSE pulses can be delivered at higher frequencies than is possible with the broader TENS pulses (typically 50–500 μs). Typically it is possible to use signals having a frequency up to about 250 kHz. We have made the unexpected discovery that the higher the frequency we deliver to the patient with TSE, the more rapid the onset of analgesia; for example frequencies in the region of 150 KHz produce analgesia within 5–30 minutes, whereas 100 Hz takes 40–60 minutes. The analgesia obtained in this way indicates a novel mode of action, as the frequency and pulse width employed in TSE lie outside the limits of conventional nerve stimulation.

Referring to the circuit diagram in FIG. 1, gates GI and G2 form an astable multivibrator whose mark-space ratio is determined by the diodes D1 and D2 and their associated components. VR2 controls the duration of the output pulse which drives the Darlington pair comprising transistor Q1 and Q2. Q2 feeds a voltage step-up transformer the secondary of which is connected via rectifier diode D4 to a 1 μF DC charge storage capacitor. Since VR2 controls the energy supplied to the primary of the step-up transformer, it controls the transformer's output and thus the amplitude of the output pulse.

The pulse train appearing at the output of the stimulator is determined by gates G3, G4, G5, G6 and the associated circuitry. Gates G3, G4 and the associated RC network comprise an astable multivibrator producing a square wave running at 100 Hz. Gates G5 and G6 comprise a monostable multivibrator circuit whose pulse width can be set by variable resistor VR1 and whose output is triggered by the 100 Hz input coming from the previously described astable circuit. The output at gate 6 therefore provides narrow pulses variable between approximately 4 and 10 μs appearing at intervals of 10 ms.

These pulses drive transistor Q3 which is an emitter follow buffer stage. This stage drives the output MOSFET device Q4. A 1 mH inductance is used as the emitter load for Q3 to preserve the shape of the output pulse driving Q4. Q4 is used to switch the high voltage to the electrodes. The 1 mH choke in parallel with the output preserves the fast rise and fall time of the pulse when driving capacitative loads. The diode D5 in parallel with the inductor restricts excursions during the falling phase of the pulse to approximately −0.7 V, giving a substantially monopolar pulse. In addition, the 1 mH choke in parallel with the output provides a failsafe mode of operation, in that should the output device Q4 go short circuit, thus applying the full charge to the skin electrodes, the choke will provide a short circuit at DC and very quickly pull the output low, thus protecting the patient.

The main features of this stimulator circuit are that it provides a high voltage, that is up to approximately 450V, a narrow pulse width, around 1–10 μs, and that this pulse has short rise and fall times, so that even under adverse output conditions a narrow pulse with short rise and fall times is maintained. This is useful for the kind of stimulation which we believe to be effective in producing analgesia by means of a painless form of electrical stimulation applied to the surface of the body that nevertheless produces effects in the central nervous system. In addition, the device has a safe failure mode since the patient is protected against continuous voltage at the output.

The foregoing circuitry is of course only one example, and may be modified in many ways to achieve a similar, or modified, effect. For example, a pair of output transistors arranged to switch a positive and a negative (with respect to ground) supply line respectively could, when driven appropriately, be made to produce mono and/or bipolar rectangular pulses of narrow width. While a pulse interval of 10 ms may be provided, giving a pulse frequency of about 100 Hz, the design may be modified to produce higher frequencies. Likewise, the pulse width can be varied in the region of 10 µs or less in the exemplified apparatus. Similarly the variable voltage output can be arranged to extend higher than 450V if desired.

In addition, the placement of a capacitor in series with one of the electrodes serves to isolate the patient from the possibility of direct current stimulation, which results from a build-up of voltage across the output inductor and can cause electrolytic lesions. This effect becomes more important at high frequencies, eg 150 kHz and above. The series capacitor together with the load impedence presented by the patient form a differentiator circuit and a bipolar differential rectangular wave appears at the electrodes. Such an arrangement is very effective in producing analgesia, with the advantage that treatment time is reduced (eg to less than 5 minutes) as it is possible to use high frequency pulses.

2. Experimental

Surface electrodes were attached to the stimulator that produced a square wave pulse of 4–8 µs duration, at a rate of 100 pulses per second, at various amplitudes (voltages), to see whether the phenomenon of spatial summation could be produced in the spinal cord.

In the following description, the conventional notations for the spinal column will be used, namely: L1–L5 are the five lumbar vertebrae, T1–T12 are the twelve thoracic vertebrae, and C1–C7 are the seven cervical vertebrae; furthermore in adult man the spinal cord descends from the base of the brain in the cervical region and reaches only as far down the spine as T12, where it rapidly tapers to a point at the lower border of L1, there to give off a sheaf of roots of the lower spinal nerves called the cauda equina that descends further down the spinal canal.

When two 4×4 cm electrodes were placed close together anywhere on the mid-line of the back over the spine from T1 downwards, a tingling sensation only was produced.

However, if the electrodes were separated by a distance of 10 cms or so the levels between T1 and T12 could be perceived and described by the trained observer at a lower threshold than the tingling. It was a continuous feeling of warmth and painless, light pressure. However, this sensation is so mild in intensity, that many patients distracted by their aches and pains are unable to perceive it. Nevertheless amongst those that report this sensation, the most striking observation about it is its continuity; the discrete sensations produced by each pulse are not detectable, as it is when tingling is present. This new feeling may be called 'spinal cord sensation' as it is only obtained when the electrodes are placed in the immediate vicinity of the spinal cord itself.

It could not be obtained anywhere else on the body. We tried but failed to obtain it by placing electrodes over the median nerve in the forearm or over the anterior trunk or over the length of the left 6th intercostal nerve. This feeling was not obtainable, when the electrodes were placed over the spine from L2 downwards. Here the electrodes lay not over the cord however, but the spinal nerve roots lying in the cauda equina. If the electrodes were placed between the levels of T1–T12 but a few cms from the mid-line of the back, the spinal cord sensation was still obtainable; but if one moved out a hand's breadth (say ca 11 cm) laterally from the spine then the feeling was lost. When the electrodes were located over the spinal cord, amplitudes capable of producing the spinal cord sensation were always lower than those capable of producing tingling sensation provided the stimulation was continuous and had a fast rise and fall time. This will be seen from the following two experiments where the anode was placed at T1, and the cathode at T12. In these examples the frequency was 100 Hz.

In the first experiment, TSE pulses that were near rectangular in shape and had both fast rise and fall times were investigated. The effects of continuous stimulation were compared with those engendered by intermittent 4ms trains of pulses with 6 ms rest periods so that each train is repeated one hundred times a second. The amplitude was increased slowly to determine at what voltage spinal cord sensation and tingling could be perceived: it could only be perceived during continuous stimulation.

As the pulse width increased in duration the thresholds of spinal cord sensation and tingling became closer. At 10 µs there was scarcely any difference between the two.

In the second experiment, a pulse of a different shape was employed a fast rise time was maintained. However, the near rectangular shape was not present and the fall time decayed exponentially. Again continuous stimulation was compared with intermittent. Spinal cord sensation was not observed with either.

First Experiment: TSE Pulse With Fast Rise and Fall Times.

| Pulse Width | CONTINUOUS STIMULATION | | INTERRUPTED STIMULATION | |
|---|---|---|---|---|
| | Threshold Spinal cord Sensation | Threshold Tingling Sensation | Threshold Spinal Cord Sensation | Threshold Tingling Sensation |
| µs | V | V | V | V |
| 2 | 96 | 118 | — | 98 |
| 4 | 46 | 65 | — | 55 |
| 6 | 29 | 40 | — | 38 |
| 8 | 28 | 32 | — | 28 |
| 10 | 22 | 23 | — | 22 |

Second Experiment: non-TSE Pulse With Fast Rise and Exponential Fall Times.

| Pulse Width | CONTINUOUS STIMULATION | | INTERRUPTED STIMULATION | |
|---|---|---|---|---|
| | Spinal Cord Sensation | Tingling Sensation | Spinal cord Sensation | Tingling sensation |
| µs | V | V | V | V |
| 2 | — | 43 | — | 35 |
| 4 | — | 32 | — | 31 |
| 6 | — | 26 | — | 23 |
| 8 | — | 20 | — | 18 |
| 10 | — | 17 | — | 16 |

Increased spinal cord sensation when the distance between the electrodes was increased We found very surprisingly that provided the electrode that comprised the cathode was placed below the anode, the amplitudes required to produce spinal cord sensation were reduced. the greater the separation between the electrodes. To support this observation. we tried to blind our study as much as possible.

Two pairs of electrodes were placed on the mid-line of the back: one pair was arranged with its electrodes on T1 and T12. while the other pair was arranged with its electrodes placed at various distances apart. but never as far apart as the first pair. Indeed the electrodes of the second pair were always placed between those of the first pair (i.e. between levels T3–T7).

The cables from the first pair of electrodes were deliberately muddled up by the experimenter. and the subject tried first one cable and then the other in a blind fashion to see which cable (when inserted into the stimulator) produced the most spinal cord sensation.

Surprisingly. it was very difficult to locate the segmental level of the sensation once it was felt. However on all occasions. the electrodes separated from each other by being placed at T1 and T12 produced more sensation than the pair of electrodes placed closer together at a given amplitude.

Provided TSE is employed with the cathode being placed below the anode in regions that overlie the spinal cord. the further apart the electrodes are placed. the lower the amplitude is required to produce this unusual continuous spinal cord sensation. However. as expected. when the amplitude of TSE (at frequencies less than 800 Hz) is increased sufficiently to start exciting $A\beta$ fibres to cause a tingling sensation. this is less likely to occur at any given voltage the further apart the electrodes are placed. For example when employing one pair of 4×4 cm electrodes disposed over the mid-line of the back. the following amplitudes were recorded at a pulse width of 4 µs and a frequency of 100 Hz:

| | Electrode size: 4 × 4 cm | |
|---|---|---|
| Electrode | Amplitude: volts | |
| location | Spinal cord sensation | Tingling sensation |
| T1, T2 | not obtainable | 84 |
| T1, T6 | 76 | 96 |
| T1, T12 | 70 | 100 |

Effects of broadening the pulse width

Then we investigated what happened if we broadened the pulse width. As one would expect the thresholds of both spinal cord sensation and tingling dropped as the pulse was broadened. On this occasion. we recorded not only spinal cord sensation. but also the pain thresholds of tingling.

| | Electrode size: 4 × 4 cm | | |
|---|---|---|---|
| | | Amplitude (volts) | |
| Electrode location | Pulse width (µs) | Spinal cord sensation | Pain threshold tingling sensation |
| T1, T12 | 4 | 100 | 220 |
| T1, T12 | 8 | 60 | 110 |

Effects of treatment

We then considered what would happen if spinal cord sensation was maintained for 10 minutes on a patient. He had a painful right knee for the past three weeks. associated with a tender medial ligament. An instrument called an algometer (that measures pressure exerted by the examiner on the patient's skin in $kg/cm^2$) was used to measure the mechanical pain thresholds. not only on the injured right knee but also the unaffected side.

Stimulation parameters: Size of electrodes: 2×4 cm;

Location of electrodes: T1, T12;

Time of stimulation: 10 minutes

Amplitude: 225 volts and Pulse width: 4 µs

Results

| | Mechanical pain threshold ($kg/cm^2$) | |
|---|---|---|
| Knee | before stimulation | after stimulation |
| Right (injured) | 1.1 | 3 |
| Left (unaffected) | 3.5 | 2 |

Thus within ten minutes treatment. the injured knee that had been 3.18 (3.5/1.1) times more tender than the unaffected side. became 0.66 (⅔) times less tender.

Conclusion

We may assess the beneficial effect as associated with well spaced electrodes over the spinal column. preferably no lower than T12. and for practical reasons it is usually difficult to attach an electrode to the body higher than T1; but these effects may still be obtained. if the upper electrode(s) are attached to the cervical or cranial regions. The pulse width is likely to be in the range of 1–10 µs. The voltage need not be sufficient to cause tingling associated with $A\beta$ fibre excitation; thus it may be subthreshold for the selected pulse width. Preferably. the voltage with be less than 1 kV.

At 600 Hz typically up to about 250V may be employed to produce analgesia at a 4 µs pulse width; but this voltage may need to be higher for a narrower pulse width. and could be lower for a broader width. At higher frequencies. unwanted heated effects begin to occur. so the voltage has to be decreased; for example. with a 1.5 µs pulse width and a frequency of 5 KHz, 150V are sufficient. while at 150 KHz a voltage of 25V was found to be effective.

The pulse shapes considered so far are monopolar. however bipolar pulses have been found to also produce analgesia. The latter may be useful in reducing electrolytic effects. As mentioned above. the electrolytic effects can be reduced by placing a capacitor in series with one of the electrodes.

The electrodes may be separate and individually applied to the skin. but for convenience. particularly to enable the patient to use the apparatus without help. they may be incorporated into a harness which the patient can wear. and adjust so that the electrodes make proper contact with the skin overlying the desired spinal column regions. If required. the electrodes may be implanted in the body either in tissues near the spine or within the spinal canal itself.

The Effects of TSE

Mechanical pain pressure thresholds may be obtained by a spring loaded probe (called an algometer) and are measured in $kg/cm^2$ (Reeves et al. 1986).

TSE stimulation tends to raise the mechanical pain pressure thresholds in tender regions of the body. whereas it may reduce the pain pressure thresholds in the previously non-tender regions.

In the case of unilateral injuries. when the tenderness of the injured area on one side was compared with the same (uninjured) region on the other side, ratios of non-tender/tender region pain pressure thresholds tend to be reduced by TSE to unity (p<0.001).

If a patient is in a good deal of pain in a particular region on one side of the body only, the tender or injured region has a low mechanical pain threshold, usually 1 kg/cm$^2$ or less, whereas the threshold on the opposite (uninjured) side of the body is usually 2 kg/cm$^2$ or more. Thus, if we take a ratio of the non-injured/injured mechanical pain thresholds, it will often be 2 or more.

Following 40 minutes or so TSE therapy, however, this ratio tends to be reduced to 1. At relatively low TSE frequencies, the mechanical pain threshold in the injured region rises, whereas the pain threshold in the non-injured regions falls. But at higher frequencies, the onset of analgesia is more rapid, and there is a tendency for the thresholds to rise in both regions: but the threshold in injured region rises at a faster rate than in the non-injured.

Studies of this kind, carried out on patients who only have a tender region on one side of the body has led to an unexpected discovery. Before treatment, sensitivity to light touch (measured with von Frey hairs (von Frey, 1896)), two point discrimination, warmth (measured by applying two equally warm steel rods on the body), and pin-prick (measured with weighted needles (Chan et al, 1992)) is reduced in the tender myofascial region, as compared with the non-tender.

Following a 40 minute period of TSE, however, these differences tend to disappear. The mechanical threshold in the injured area is raised, while the thresholds to all other types of sensation fall to the levels found on the uninjured side.

Despite the fact that the electrodes are always located over the spinal cord, these changes occur wherever the tender region lies, be it in the foot, hip, back, wrist shoulder or head or all of these regions simultaneously.

These observations suggest that TSE produces pain relief without introducing numbness in the manner of local anaesthesia. TSE tends to have the opposite effect of local anaesthesia and following this therapy, although the tenderness has been reduced, the patient's perception of pin-prick, warmth, light touch and ability to discriminate between two points tend to be heightened in the injured area.

When pain relief occurs as a result of TSE, one may observe a temporary but generalised vasodilatation (a warming up of the skin caused by relaxation of vascular tone usually brought about by a reduction in sympathetic activity that normally accompanies pain relief).

Apart from these findings, we have not observed any other changes. No numbness or loss of motor power occurs. There are no changes in reflexes, pulse rate or blood pressure. In common with the TENS and dorsal column stimulation, that has been used for the past two decades, there appear to be no known side effects from this type of stimulation.

Clinical Studies

In all the clinical studies detailed below TSE was carried out with two electrodes placed over the spinal cord.

In a study of 23 patients suffering from a number of painful, chronic, subacute and acute conditions, TSE produced an average of 70% pain relief for an average of 50 hours following the first treatment of no more than 45 minutes stimulation. These results are set out in table 1 on pages 22 and 23. Here a 4 μs pulse width was employed at a frequency of 100 Hz. The voltage was increased in each case to try and produce a spinal cord sensation at approximately 180V. In those patients who were unable to perceive the spinal cord sensation, the voltage was increased until they just began to experience a tingling sensation, which experiments have shown to be more than sufficient to cause spinal cord sensation in those who can perceive it.

The effects of repeated TSE therapy were then investigated in a further group of 50 consecutive chronic pain sufferers (see table 2).

When the results for the first 100 consecutive patients were analysed, 63% of these patients, who had painful conditions of relatively recent origin (on average 2.6 years) required 3–5 treatments to produce a 60% or more subjective relief of pain during the treatment period. These patients appeared to derive a cumulative effect, ie it was found that when each treatment is repeated, the duration of relief provided tended to be longer.

However, 30% of these patients, who had more severe, long lasting conditions (on average of 12 years duration) did not benefit from this accumulative effect. To remain comfortable they required TSE to be repeated daily or every other day. However, as the location of the TSE electrodes are standardised, it is not difficult for relatives or carers or even the patient himself to continue TSE at home.

Surprisingly, if patients with conditions as neuro- or psychogenic pains are excluded, only 7% of these severely affected patients did not obtain pain relief from TSE. This very low figure compares with the 60% failure rate of TENS.

Those patients who invariably fail to derive any form of relief from TSE tend to have very severe pain associated with mechanical spine disorders. These patients are often bed-bound and are usually awaiting orthopaedic or neurosurgical procedures. Often the skin has developed a hyperaesthesia (sensitivity to light touch) over large regions of the body. Other conditions that are associated with hyperaesthesia such as post-herpetic neuralgia also do not respond well. However, we have found that reversing the polarity of the electrodes appears to give some short term relief of hyperaesthesia.

The patients whose conditions responded well to treatment were those who are reasonably mobile and suffer more common pains that are not associated with pressure on nerve roots. Chronic myofascial or osteoarthritic pains in almost every region of the body such as knees, elbows or shoulders, also tend to do well with the electrodes placed at T1 and T12. For pains arising in the head itself, however, such as chronic sinusitis, jaw or dental pain, we found that the most effective location of electrodes were either side of the neck in the vicinity of the cervical segments of the cervical cord.

TSE has provided pain relief to those patients who have fibromyalgia, ME or post-viral disorders where they have pains in many regions simultaneously. However their feelings of fatigue were found to remain.

Chronic post-injury or post-operative pains tend to do well. But acute or active arthritic pains such as rheumatoid arthritis also may respond but to a much lesser degree.

In all these cases, regardless of the site of pain or the number of such sites, the electrodes are merely placed over the spinal cord.

Controlled Clinical Trial

A controlled clinical trial of TSE has been carried out. It received approval from the United Bristol Hospital Trust Research Ethics Committee. It was a randomised double-blind, cross-over study of the pain relieving effects of TSE versus TENS in patients suffering chronic pain of musculoskeletal origin.

Eight consecutive 'stably unwell' adult patients, who had intact nervous systems and a duration of daily musculoskeletal noninceptive (as opposed to neurogenic or psychogenic) pain for a year or more were studied. Their average age was 55 years, and the average duration of continuous pain was 12.4 years; their average physical disability index (Fairbank et al (1980)) or incapacity was 52.8 percent (0%, no incapacity; 100%, total incapacity).

Provided that various exclusion criteria did not apply, the patients were randomly assigned to one of two groups—TSE or TENS, in a double-blind cross-over manner, so that on one occasion a patient might receive TENS and on the next TSE, or vice versa.

Special apparatus was constructed, so that TSE or TENS could be applied in such a way that only an external trial coordinator knew which treatment was being applied on any particular occasion. In both cases the stimulation was supplied to electrodes placed over the skin overlying the spinal cord.

Neither the practitioner nor the patient was aware of which type of treatment was actually in use on any occasion. In this way the patients acted as their own controls, and received both types of treatment in a random, 'double-blind' order.

As pain is so difficult to quantify, the following six measures of efficacy of each type of treatment were studied.

Short Form McGill questionnaires (Melzack, 1987) were used to indicate the severity of pain before and after each treatment. A pain reduction score (0, no reduction; 100, complete reduction) and the number of hours this lasted after each type of treatment gave an important indication of the success or otherwise of each form of therapy. Changes in physical signs (including measurements of tenderness by algometry) and their severity, and the number and size of tender regions gave further indication of the effects of each type of treatment.

For the purpose of this clinical trial, each patient needed to attend for two hour periods at four weekly intervals.

Statistical analysis was performed by the non-parametric Wilcoxon rank sum test to compare the results obtained by TSE with TENS.

Four out of the six measures of efficacy revealed the probability that these two treatments were equally effective was less than 0.5% (ie p<0.005). In the remaining two measures of efficacy the probability was less than 1% (ie p<0.01).

When all the measures of efficacy were combined the effects of TSE was shown to be significantly superior to TENS (p<0.005).

REFERENCES

Brinley F. J. (1974), Excitation and conduction in nerve fibres. In: Medical Physiology (vol 1). Ed: Mountcastle VB. 13th Ed. The Cv Mosby Co, pp 34–76.

Chan A. W., MacFarlane I. A., Bowsher D., Campbell J. A. (1992), Weighted needle pin prick thresholds, a simple test of sensory function in diabetic peripheral neuropathy. J. Neurol. Neurosurg. Psychiat. 55, 56–59.

Fairbank J. C. T., Couper-Mboat J., Davies J. B. and O'Brien J. P. (1980), The Oswestry low back pain disability questionnaire. J. Physiotherapy 66, 271–273.

Krainick J.-U., Thoden U. (1989), Spinal cord stimulation. In: The Textbook of Pain. Eds: Wall P. D., Melzack R. 2nd Ed. Churchill Livingstone, pp 920–924.

Li C. L., Bak A. (1976) , Excitability characteristics of the A- and C-fibres in a peripheral nerve. Exp. Neurol. 50, 67–79.

Melzack R., Wall P. D. (1965), Pain mechanisms: a new theory. Science (150) 971–979.

Melzack R. (1987) , The short-form McGill Questionnaire. Pain 30, 191–197.

Reeves J. L., Jaeger B. and Graff-Radford S. B. (1986), Reliability of the pressure algometer as a measure of myofascial trigger point sensitivity. Pain 24, 313–321.

Stinus L., Auriacombe M., Tignol J., Limoge A., Le Moal M. (1990), Transcranial electrical stimulation with high frequency intermittent current (Limoge's) potentiates opiate-induced analgesia: blind studies. Pain 42, 351–363.

von Frey M. (1896), Untersuchungen uber die Sinnesfunctionen der Menschlchen haut erste abhandlung:druckempfindung und schmerz. Abhandlung der Sachsischen Akademie der Wissenschaften 23, 169–266.

Wall P. D. (1986), The discovery of Transcutaneous Electrical Nerve stimulation. Journal of Orthopaedic Medicine 3, 26–28.

Woolf C. J. (1989), Segmental afferent fibre-induced analgesia: transcutaneous electrical nerve stimulation (TENS) and vibration. In: The Textbook of Pain. Eds: Wall, P. D., Melzack R. 2nd Ed. Churchill Livingstone, pp 884–896.

TABLE 1

RESULTS OF FIRST TSE TREATMENT on a group of 23 patients

| No | Sex | Severity (0 nil - 10 agony) | Duration (months) | Diagnosis | % Relief (0 nil-100 total) | Duration of relief (hrs) |
|---|---|---|---|---|---|---|
| 1 | F | 7 | 3 | Hip Pain | 50 | 72 |
| 2 | F | 8 | 180 | Fused C5/6 | 50 | 2 |
| 3 | M | 5 | 240 | Polymalgia rheumatica | 50 | 16 |
| 4 | F | 9 | 3 | Shoulder pain | 50 | 4 |
| 5 | F | 3 | 1 | TMJ (jaw) pain | 60 | 17 |
| 6 | M | 3 | 0.5 | Ankle pain | 20 | 24 |
| 7 | F | 5 | 0.5 | Foot pain | 80 | 12 |
| 8 | F | 3 | 4 | RA hand | 100 | 70 |
| 9 | F | 8 | 132 | Cervical spondylosis | 100 | 120 |
| 10 | F | 4 | 360 | RA feet, wrists | 50 | 2 |
| 11 | F | 4 | 84 | Sarcoid, back abdomen & shoulders | 50 | 168 |
| 12 | F | 6 | 21 | Back pain | 50 | 1.5 |
| 13 | M | too distressed to give an opinion as to severity | 0.04 | Post-op pain resection of lower 1/3rd oesophagus | 100 | 7 |
| 14 | F | 5 | 6 | Cervical spondylitis | 75 | 96 |

TABLE 1-continued

RESULTS OF FIRST TSE TREATMENT on a group of 23 patients

| No | Sex | Severity (0 nil - 10 agony) | Duration (months) | Diagnosis | % Relief (0 nil-100 total) | Duration of relief (hrs) |
|---|---|---|---|---|---|---|
| 15 | F | Aged 92: unable to quantify pain numerically - described it as 'nasty'. | 9 | Cervical spondylitis | Better | 120 |
| 16 | M | 4 | 1 | 2° Ca spine | 100 | 96 |
| 17 | F | 6 | 5 | L5/S1 PID | 50 | 120 |
| 18 | F | 2 | 12 | Achilles tendonitis | 80 | 72 |
| 19 | M | 8 | 0.001 | Ischaemic pain in the calves - running while unfit | 90 | NFP |
| 20 | M | 10 | 1 | Collapse of vertebral body c steroid therapy | 90 | 9 |
| 21 | M | 2 | 120 | Cervical spondylitis | 80 | 24 |
| 22 | F | 3 | 3 | Shoulder pain | 100 | 72 |
| 23 | F | 8 | 0.03 | Fractured humerus | 90 | 48 |
| Average | | 5 | 56 | | 71 | 53 |

Key: NFP no further pain; RA rheumatoid arthritis; c associated with; 2° secondary carcinomatous deposits.

TABLE 2

The number of TSE treatments required to produce a successful outcome in the next 50 consecutive patients.
Key:
c means associated with
OA means osteoarthritis
RTA road traffic accident
Success means pain relief at 60% or more (0, no relief; 100, complete relief)

| No | Condition | years duration | number of treatments required for long term success | contd treatment reqd |
|---|---|---|---|---|
| 24 | Tennis Elbow | .2 | 3 | |
| 25 | Low back pain | .25 | 3 | |
| 26 | Knee pains | 1.5 | 5 | |
| 27 | Ovarian carcinoma | 1.25 | | daily |
| 28 | Hip pain | .75 | 5 | |
| 29 | Osteoporotic collapse of vertebra c steroid therapy | .5 | | daily |
| 30 | OA cervical spine and wrists | 12.0 | 4 | |
| 31 | Post-viral fatigue & post-operative cardiac bypass pain | 3.0 | 12 | |
| 32 | Shoulder pain | .5 | 3 | |
| 33 | Post-operative pain (cholecystectomy) and a fall fracturing ribs | 4.25 | 2 | |
| 34 | Rheumatoid arthritis wrist and hands | .75 | 3 | |
| 35 | Post-operative eye pain c correction of squint & drug addiction | 5.25 | 10 | |
| 36 | Posterior thoracic pain & anxiety depression | 8.0 | 7 | |
| 37 | Leg pains following episode of Guillain-Barré syndrome | 4.5 | 4 | |
| 38 | Neck pains c osteoporotic collapse of T1 | 1.5 | 5 | |
| 39 | Generalised pains c sarcoid | 12.0 | 5 | |
| 40 | Generalised pains c Parkinson's disease | 10.0 | | daily |
| 41 | Neck and low back pain c 3 prolapsed disc injuries | 5.0 | | daily |
| 42 | OA neck and lumbar spine | 11.0 | 8 | |
| 43 | Leg pains & headache c anxiety | 15.0 | | alternate days |
| 44 | Carcinomatous deposits in spine | 2.0 | | daily |
| 45 | Elbow and shoulder pain | .25 | 2 | |
| 46 | Dysmenorrhoea | 4.0 | | once a month |
| 47 | Cervical | 10.0 | 5 | |

TABLE 2-continued

The number of TSE treatments required to produce a
successful outcome in the next 50 consecutive patients.
Key:
c means associated with
OA means osteoarthritis
RTA road traffic accident
Success means pain relief at 60% or more (0, no relief;
100, complete relief)

| No | Condition | years duration | number of treatments required for long term success | contd treatment reqd |
|---|---|---|---|---|
| | spondylosis | | | |
| 48 | Severe generalised pains following a fall - compensation sought | 0.75 | 3 | |
| 49 | Hip pain c lumbar spine degeneration | 4.5 | | once a month |
| 50 | Heel pain | 2.0 | | Once a week |
| 51 | Post-operative pain following knee replacement | 0.5 | 3 | |
| 52 | Neck pain following Cloward's fusion | 1.5 | 3 | |
| 53 | Generalised joint pains | 0.01 | 3 | |
| 54 | Migrainous neuralgia | 10.0 | | Twice daily during episodes |
| 55 | L4/5 disc requiring surgery | 0.025 | failed | |
| 56 | Posterior thoracic pain c OA cervical spine | 3.25 | 3 | |
| 57 | C5/6 disc requires surgery | | | daily |
| 58 | L4/5, L5/S1 disc requires surgery, compensation sought | 5.5 | | daily |
| 59 | Athlete with back and leg pains | 0.5 | 4 | |
| 60 | Heel Pain | 2.0 | 5 | |
| 61 | Post-viral fatigue c generalised pain | 3.0 | | twice a week |
| 62 | Osteoporotic collapse of T3 | 2.5 | 4 | |
| 63 | Hip pain following a fall from scaffolding | 4.5 | 5 | |
| 64 | Polymyalgia rheumatica | 5.5 | | daily |
| 65 | Throat pain c radiotherapy of larynx & morphine addiction | 2.5 | | daily |
| 66 | Cervical spondylosis following RTA | 12.0 | | once a week |
| 67 | Post-herpetic neuralgia | 1.0 | failed | |
| 68 | Pain in posterior thoracic region | 0.5 | 2 | |
| 69 | Pain in shoulder following a fall | 0.25 | 4 | |
| 70 | OA knees and cervical spine | | | once a week |
| 71 | Migraine | 12.0 | | daily |
| 72 | OA neck c arm pain | 25.0 | | once a week |
| 73 | Trigeminal neuralgia | 0.5 | 1 | |

We claim:

1. Apparatus for inducing analgesia in a patient by applying electrical pulses to the patient's body, the apparatus comprising two or more electrodes for supplying electrical pulses to two or more locations on the patient's body overlying the central nervous system, and generating means connectable to the electrodes, wherein the generating means provide continuous electrical pulses, having a pulse width of 10 μs or less and a frequency of greater than 100 Hz, to the electrodes on the patient's body, the pulses having an amplitude greater than 50V, so that analgesic effects are induced in the central nervous system, while stimulating peripheral nerves that lie between the electrodes and the central nervous system to a lesser extent or not at all.

2. The apparatus of claim 1, wherein the pulses have an amplitude of 180V or more.

3. The apparatus of claim 2, wherein the pulses have an amplitude between 450V and 1 kV.

4. The apparatus of claim 1, wherein the pulse width is between 1.5 and 4 μs.

5. A method of inducing analgesia in a patient's body using electrical pulses, the method comprising:

applying two or more electrodes to the surface of the patient's body overlying the central nervous system; and providing continuous electrical pulses, having a pulse width of 10 μs or less and a frequency of greater than 100 Hz, to the electrodes on the patient's body, the pulses having an amplitude greater than 50V, so that analgesic effects are induced in the central nervous system, while stimulating peripheral nerves that lie between the electrodes and the central nervous system to a lesser extent or not at all.

6. A method of inducing analgesia in a patient's body using apparatus comprising two or more electrodes for supplying electrical pulses to two or more locations on the patient's body overlying the central nervous system, and generating means connectable to the electrodes, the method comprising:

applying the electrodes to the surface of the patient's body overlying the central nervous system; and using the generating means to provide continuous electrical pulses, having a pulse width of 10 μs or less and a frequency of greater than 100 Hz, to the electrodes on the patient's body, the pulses having an amplitude greater than 50V, so that analgesic effects are induced in the central nervous system, while stimulating peripheral nerves that lie between the electrodes and the central nervous system to a lesser extent or not at all.

7. The method of claim 6, wherein the electrodes are applied to the patient's body overlying the spinal cord between T1 and T12 vertebrae.

8. A method of inducing analgesia in a patient's body using apparatus comprising two or more electrodes for supplying electrical pulses to two or more locations on the patient's body overlying the central nervous system, and generating means connectable to the electrodes, the method comprising:

applying the electrodes to the surface of the patient's body overlying the spinal cord between T1 and T12 vertebrae; and using the generating means to provide continuous electrical pulses, having a pulse width of 10 μs or less and a frequency of greater than 100 Hz, to the electrodes on the patient's body, the pulses having an amplitude greater than 50V, so that analgesic effects are induced in the central nervous system, while stimulating peripheral nerves that lie between the electrodes and the central nervous system to a lesser extent or not at all.

* * * * *